United States Patent [19]

Weissman

[11] 4,349,335
[45] * Sep. 14, 1982

[54] OVAL DENTAL ANCHOR

[75] Inventor: Bernard Weissman, New York, N.Y.

[73] Assignee: Ipco Hospital Supply Corporation, White Plains, N.Y.

[*] Notice: The portion of the term of this patent subsequent to Jun. 29, 1997, has been disclaimed.

[21] Appl. No.: 77,400

[22] Filed: Sep. 20, 1979

Related U.S. Application Data

[63] Continuation-in-part of Ser. No. 845,628, Oct. 26, 1977.

[51] Int. Cl.³ .............................................. A61C 5/04
[52] U.S. Cl. .................................................. 433/225
[58] Field of Search ....................... 433/225, 211, 174; 85/41, 46, 47

[56] References Cited

U.S. PATENT DOCUMENTS

| | | | |
|---|---|---|---|
| 2,413,333 | 12/1946 | Myerson | 433/211 |
| 2,414,870 | 1/1947 | Harding | 151/22 |
| 3,398,625 | 8/1968 | Ansingh | 85/46 |
| 3,499,222 | 3/1970 | Linkow et al. | 433/174 |
| 3,537,288 | 11/1970 | Ansingh | 72/88 |
| 3,861,043 | 1/1975 | Lieb et al. | 433/225 |
| 3,928,915 | 12/1975 | Ellman | 433/225 |
| 4,171,569 | 10/1979 | Rovins | 433/225 |
| 4,189,834 | 2/1980 | Smith | 433/225 |

FOREIGN PATENT DOCUMENTS 905714 7/1972 Canada .............................. 433/225

Primary Examiner—Gene Mancene
Assistant Examiner—John J. Wilson
Attorney, Agent, or Firm—Friedman, Goodman & Teitelbaum

[57] ABSTRACT

A dental anchor is disclosed comprising an elongated body member for insertion into a channel in a tooth in order to anchor a superstructure to the tooth. The body member has at least one section with a substantially oval cross-sectional configuration having a major axis and a minor axis. The at least one section is provided with self tapping threads for threading into the channel. The threads have a root diameter less than the minor axis dimension of the oval configuration and a crest diameter at least equal to the major dimension of the oval configuration. Preferably, the body member includes two similar sections joined together by a reduced thickness portion so that one section can be bent relative to the other section when seated in the channel to provide an anchoring portion for the superstructure. Two dental anchors may be joined together by a reduced thickness frangible member, where the thickness of the reduced thickness portion of each dental anchor has a thickness greater than any thickness of the frangible member. Accordingly, the longer sides of the dental anchor are spaced from the walls of the channel when the anchor is seated in the channel to thereby relieve the stress on the tooth when threading the anchor into the channel. Additionally, it provides spaces therebetween, so that if cement is used it can be disposed in these spaces.

4 Claims, 5 Drawing Figures

OVAL DENTAL ANCHOR

BACKGROUND OF THE INVENTION

The present invention is a continuation-in-part application of Ser. No. 845,628 filed Oct. 26, 1977 by the applicant.

The present invention relates to dentistry in general, and more particularly to an improved dental anchor for building superstructures on broken or undermined dentition.

Anchoring a superstructure to the understructure of a tooth usually requires drilling a number of channels into the tooth or understructure. Depending upon the tooth involved, one or more anchoring rods are then secured in the channels and are allowed to protrude above the understructure with the exposed or protruding portions of the rods serving to anchor the superstructure. It should be noted, that in this type of dental operation, these rods are extremely small, for example, being on the order of 0.03" in diameter and approximately 0.20" in length.

The rods are retained in the channels by (1) cementation, by (2) being screwed into the channels, or by (83) friction lock where the rod is forced into a channel of smaller diameter. According to tensile tests performed on rods secured in dentin, self-threading rods have the greatest retention of the three types tested, where the friction lock is classified as intermediate, and the cemented rod is the least retentive.

It is noted, that prior art dental anchors are disclosed in my U.S. Pat. No. 3,434,209 showing a structure of a single dental anchor, and my U.S. Pat. No. 3,675,328 showing two dental anchors interconnected to one another which are readily severable from one another.

It is noted, that stresses are normally present when inserting the prior art dental anchors into the channels. Additionally, the construction of the prior art dental anchors require torque for insertion thereof into the channels provided in the tooth.

The aforementioned Ser. No. 845,628 provides one embodiment of the invention where the dental anchor has a substantially square cross-section to provide four longitudinal side surfaces joined by four longitudinal corner portions. Each of the corner portions are provided with threads for self-tapping the one section into the channel when the body member is rotated about its longitudinal axis.

Another prior art dental anchor and method for securing the anchor in a channel described in U.S. Pat. No. 3,928,915. An improved cement is described in that patent which is used in conjunction with a dental pin having a square cross-section with the corners threaded in order to provide space between the pin and the channel to receive the improved cement. The pin had square corners and only the corners are threaded with a thread having a crest diameter greater than the diagonal dimension of the square configuration in order to insure that the corners remain square. This patent does not have self-tapping threads.

SUMMARY OF THE INVENTION

Accordingly, it is an object of the present invention to provide an improved dental anchor for building a superstructure on broken or undermined dentition.

Another object of the present invention is to provide an improved dental anchor which is fixedly secured in the understructure of a tooth.

A further object of the present invention is to provide an improved dental anchor which reduces the stresses normally present when inserting the prior art dental anchors into the channels provided in the understructure of a tooth, which also reduces the torque required during this insertion.

Still another object of the present invention is to provide a dental anchor in the form of sections with substantially oval cross-sectional configurations, each having a major and minor axis, where self-tapping threads are provided around the sections, with the thread of each section having a root diameter less than the corresponding minor axis dimension of its oval configuration and a crest diameter at least equal to the major axis of its oval configuration.

Yet another object of the present invention is to provide an improved dental anchor as set forth above, wherein the side portions of the dental anchor are spaced from the walls of the channel when the anchor is seated therein to provide spaces therebetween in order to relieve the stress to the tooth during insertion of the anchor into the channel.

Still a further object of the present invention is to provide an improved dental anchor having walls which are spaced from the walls of the channel when the anchor is seated therein so that, if desired, cement can be disposed in these channels to aid in securing the dental anchor in the channel.

These objects are achieved in accordance with a preferred embodiment of the present invention, wherein the dental anchor comprises an elongated body member having at least one section with a substantially oval cross-sectional configuration having a major axis and a minor axis, the at least one section being provided with self-tapping threads for threading into the channel. The threads having a root diameter less than the minor axis dimension of the oval configuration and a crest diameter at least equal to the major axis dimension of the oval configuration. The body member includes two similar sections joined together by a reduced thickness portion so that one section can be bent relative to the other section. Preferably, two dental anchors are joined together by a reduced thickness frangible member having a thickness less than the thickness of the above mentioned reduced thickness portions of each dental anchor. When the anchor is seated in the channel, the side portions of the dental anchor are spaced from the walls of the channel to relieve the stress on the tooth when threading the anchor into the channel. Additionally, it provides spaces therebetween so that if cement is used it can be disposed in the spaces.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENT

Figure 1:
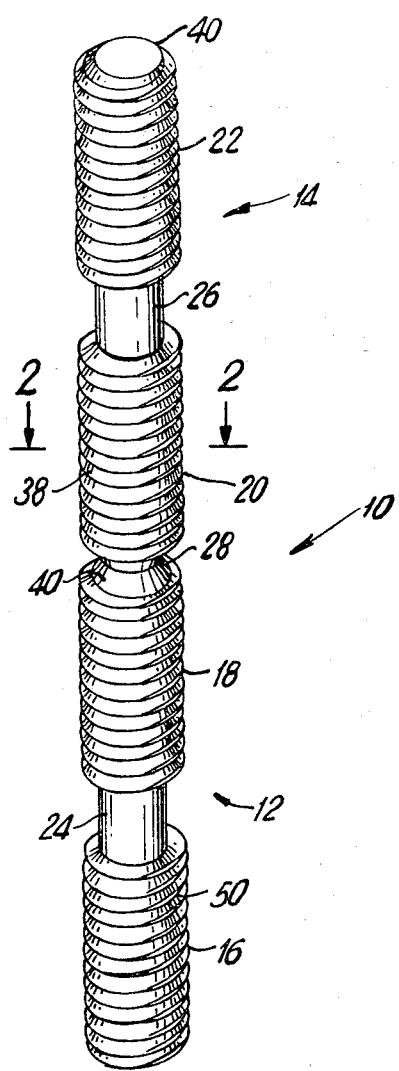
FIG. 1 is a perspective view illustrating the dental anchor comprising the present invention.

Referring now to the drawing, FIG. 1 shows a dental anchor 10 of the present invention comprising two reinforcing or anchor rods 12, 14 interconnected to one another. However it is understood, that the present invention relates just as well to the construction of a single reinforcing or anchor rod and also to the construction of a dental anchor having more than two reinforcing or anchor rods interconnected to one another.

Each of the anchor rods 12, 14 includes first and second coaxial sections 16, 18 and 20, 22 which are joined together by intermediate reduced thickness portions 24 and 26. Additionally, section 18 of anchor rod 12 is joined to the section 20 of anchor rod 14 by a frangible reduced thickness portion 28 to define a one piece elongated dental anchor 10. The dimension of the reduced thickness portion 28 is selected such that it has a cross-sectional thickness less than that of the intermediate portions 24, 26 in order that the elongated body of the dental anchor 10 will fracture at this reduced thickness portion 28 after being inserted into a channel formed in the understructure of a tooth or dentition, in a manner as set forth in my above-mentioned patents to which reference may be made.

Figure 2:
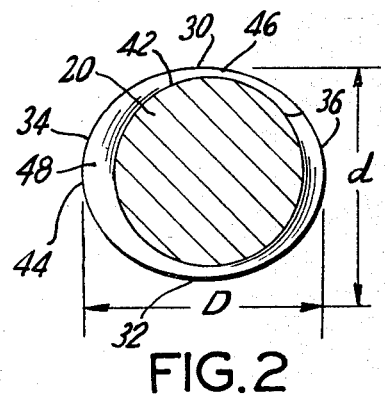
FIG. 2 is a transverse sectional view taken along line 2—2 of FIG. 1.

As shown in FIGS. 1 and 2, each of the sections 16, 18, 20 and 22 has a substantially oval cross-section having a major diameter D and a minor diameter d to provide each section with two angular side portions 30, 32 joined by two angular end portions 34, 36. The intermediate portions 24, 26 are cylindrical. Additionally, the sections 16, 18, 20 22 are provided with self tapping screw threads 38. Preferably, at least one or all of the sections 16, 18, 20 and 22 has at least one end thereof terminating in a bevelled or chamfered end 40.

The threads are formed entirely around each of the sections 16, 18, 20 and 22. The threads have a root diameter 42 which is less than the minor axis dimension d, and a crest diameter 44 which is at least equal to the major axis dimension D. In this manner, there will be two different depths of screw threads formed on the sections. At the angular side portions 30, 32 the depth of thread is small, shown at 46. At the two angular end portions, the depth of thread is larger, as shown at 48. If the crest diameter is substantially equal to the major axis dimension, then the edges of the threads at the angular end portions 34, 36 will be sharp. If the crest diameter is slightly larger than the major axis dimension, then the edges of the teeth at the end portions 34, 36 will be truncated. Since the crest diameter is naturally larger than the minor axis dimension d, the teeth at the side portions 30, 32 will be slightly flattened, as shown at 50 in FIG. 1.

Figure 3:
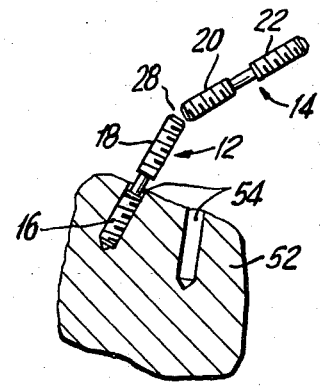
FIG. 3 is a cross-sectional view of a tooth or dentition with its surface excavated prior to building of a superstructure thereon, showing the first dental anchor inserted therein.
Figure 4:
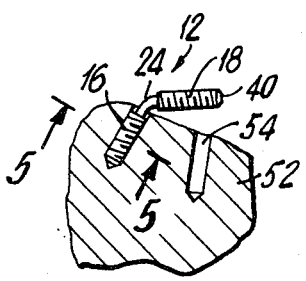
FIG. 4 is a cross-sectional view similar to FIG. 3 illustrating a bent dental anchor therein.
Figure 5:
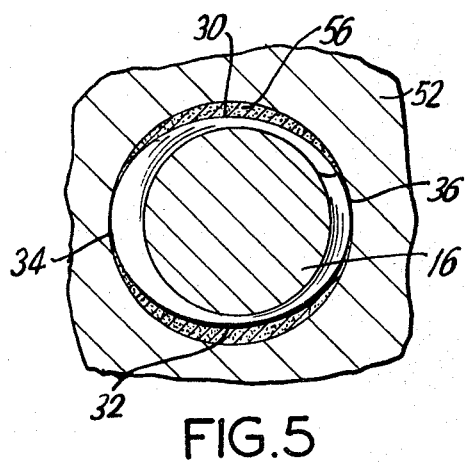
FIG. 5 is a cross-sectional view taken along line 5—5 of FIG. 4.

Referring to FIGS. 3, 4 and 5, the tooth 52 is prepared for building a super-structure thereon in the manner set forth in my above-mentioned patents, where a plurality of channels 54 having predetermined diameters are drilled therein. The dental anchors are now inserted into the channels 54, where the major axis of the oval cross-section of each anchor is greater than the diameter of each channel. The dental anchor can be rotated either by a manual tool or by a power tool attached to the end section 22. The opposite end section 16 is thus threaded into the channel 52 by application of a slight downward pressure and simultaneous rotation of the dental anchor 10 as set forth above. Thus the threads 38 are self tapped into the tooth and form complementary threads in the walls of the channel to threadably engage the dental anchor.

It is noted, that the construction of this dental anchor is such that the threads at the end portions 34, 36 will do most of the cutting into the tooth. This reduces the stresses normally present when inserting the prior art dental anchors into the channels. Additionally, the construction of the dental anchor of the present invention reduces the torque required for the insertion thereof into the channels provided in the tooth. Furthermore, it is noted that section 16 can also be provided with a chamfered end. Accordingly, either section 16 or 22 can be initially threaded into the channel, where both ends of the anchor can have the same configuration.

The threads formed around the anchor are such as to provide the best situation combining both reduced stress and improved retention. In prior art anchors, if the thread was formed around a complete circular member, the entire member would be threaded into the channel around its entire periphery causing great stress to the tooth during its self tapping. On the other hand, if only a portion were threaded, even though it would reduce the stress, there would not be provided sufficient holding power to retain the anchor in the channel. By utilizing the oval configuration with the threads formed around the entire periphery, the end portions will do most of the cutting during the self tapping into the channel. On the other hand, the side portions which are narrower will be slightly spaced from the walls of the channel to thereby relieve the stresses during self-tapping. At the same time, there will be sufficient threads around the end portions so that the anchor will be retained within the channel. In fact, for many applications there will be sufficient retaining strength so that the anchor will remain in the channel without the need for additional cement. However, where desired, cement can be placed in the channel for aiding in retaining the anchor in the channel. For this purpose, the threads formed along the side portions will be useful in providing additional holding power to hold the anchor in the cement.

Once the entire section 16 of the anchor 10 is seated in the channel 54 of the tooth 52, further rotation of the anchor will cause the frangible reduced portion 28 to break off, where the intermediate portion 24 and the rear section 18 will now protrude from the tooth as shown in the drawings. The anchor rod 14 is now ready to be threaded into a second channel 54 in the tooth in the same manner as mentioned above. The intermediate portion 24 will form a guide to aid in determining where to bend the anchor.

As shown in FIG. 4, the protruding section 18 is bent or inclined relative to the inserted section 16 to provide an anchoring portion for the superstructure, where the bending takes place along the intermediate portion 24 which has a reduced cross-section for this purpose. However, before the bending thereof, it may be desired to provide commercial available cement 56 or the like, which is well known in the art, into the channel 54. The cement 56 can be coated onto the section 16, can be inserted into the channel 54 before the insertion of the section 16, or can be applied after the insertion of the section 16, depending upon the requirements thereof.

It is noted, that the cement 56 functions to (1) seal the channel 54, (2) fixes the anchor section 16 in the channel 54, (3) prevents the anchor section 16 from turning or rotating after the cement has hardened, and (4) facilitates the bending of the dental rod by securing the dental end section 16 to the tooth 52. The threads formed on the side portions 32, 34 of the anchor will aid in holding the tooth into the cement.

In a typical embodiment of the invention, the major axis of the oval configuration was 0.030", the minor axis dimension was 0.029" the root diameter was 0.027" and the crest diameter was approximately equal to the major axis. In forming the anchor, oval stock is utilized and the threads are formed directly on the oval stock.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental anchor for insertion into channels in a tooth, said dental anchor comprising:

a first elongated body member, said first body member having at least one section with a substantially oval cross-sectional configuration having a major and minor axis to provide two angular side portions joined by two angular end portions, said at least one section being provided with thread means for self-tapping said one section into a first channel when said body member is rotated about its longitudinal axis, said thread means having a root diameter less than the minor axis dimension and a crest diameter at least equal to the major axis dimension, whereby said side portions of said one section are spaced from walls of the first channel when said one section is seated in the first channel to reduce self-tapping stresses;

a second elongated body member along said longitudinal axis, said second body member having at least another section with a substantially oval cross-sectional configuration having a major and minor axis to provide another two angular side portions joined by another two angular end portions, said another section being provided with second thread means for self-tapping said another section into a second channel when said second body member is rotated about said longitudinal axis, said second thread means having a root diameter less than the minor axis dimension of the oval configuration of said another section and a crest diameter at least equal to the major axis dimension of the oval configuration of said another section, whereby said another four side portions of said another section are spaced from walls of the second channel when said another section is seated in the second channel to reduce self-tapping stresses, and a frangible reduced thickness member connecting said body members together; and each of said body members including a second section along said longitudinal axis and a reduced thickness portion disposed intermediate said sections of each said body members to permit said second sections to be bent relative to said one section and said another section respectively after said one section and said another section are seated in their channels respectively to provide anchoring portions for a superstructure, said reduced thickness portion of each of said body members having a thickness greater than any thickness of said frangible reduced thickness member.

2. A dental anchor according to claim 1, wherein said reduced thickness portions are each cylindrical.

3. A dental anchor according to claim 1, wherein each said second section has a substantially oval cross-sectional configuration having a major and minor axis to provide two angular side portions joined by two angular end portions on each of said body members.

4. A dental anchor according to claim 3, wherein each of said second sections respectively is provided with self tapping means having a root diameter less than the minor axis dimension of its respective oval configuration and a crest diameter at least equal to the major axis dimension of its respective oval configuration.

* * * * *